(12) United States Patent
Sommer et al.

(10) Patent No.: US 11,250,590 B2
(45) Date of Patent: Feb. 15, 2022

(54) AUTOMATED DETECTION OF ABNORMAL SUBJECT CONFIGURATION FOR MEDICAL IMAGING

(71) Applicant: KONINKLIJKE PHILIPS N.V., Eindhoven (NL)

(72) Inventors: Karsten Sommer, Hamburg (DE); Sascha Krueger, Hamburg (DE); Julian Senegas, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 17/263,985

(22) PCT Filed: Dec. 12, 2019

(86) PCT No.: PCT/EP2019/084969
§ 371 (c)(1),
(2) Date: Jan. 28, 2021

(87) PCT Pub. No.: WO2020/126853
PCT Pub. Date: Jun. 25, 2020

(65) Prior Publication Data
US 2021/0312659 A1 Oct. 7, 2021

(30) Foreign Application Priority Data

Dec. 20, 2018 (EP) ..................................... 18214629

(51) Int. Cl.
*G06T 7/73* (2017.01)
*A61B 5/00* (2006.01)
*A61B 5/055* (2006.01)

(52) U.S. Cl.
CPC ................ *G06T 7/74* (2017.01); *A61B 5/055* (2013.01); *A61B 5/704* (2013.01); *A61B 5/7267* (2013.01);
(Continued)

(58) Field of Classification Search
CPC . A61B 5/055; A61B 5/70–708; A61B 5/0035; A61B 5/0077; A61B 6/04–0492; G06T 7/74
See application file for complete search history.

(56) References Cited

U.S. PATENT DOCUMENTS 10,783,655 B2 * 9/2020 Zhao ....................... A61B 6/032
10,783,660 B2 * 9/2020 Inoue ....................... G06N 3/08
(Continued)

OTHER PUBLICATIONS

Choy et al. "Current Applications and Future Impact of Machine Learning in Radiology." Radiology 2018; 288:318-328. (Year: 2018).*
(Continued)

*Primary Examiner* — Angela M Hoffa (57) ABSTRACT

The invention provides for a medical instrument (100, 400) comprising a medical imaging system (102, 402) configured for acquiring medical imaging data (432) from a subject (108); a subject support (110) configured for supporting the subject during acquisition of the medical imaging data; and an optical imaging system (114, 114') configured for acquiring optical imaging data (134) of the subject on the subject support. The execution of the machine executable instructions causes a processor (122) controlling the medical instrument to: control (200) the optical imaging system to acquire the optical imaging data; generate (202) the initial vector (136) using the optical imaging data; generate (204) the synthetic image by inputting the initial vector into a generator neural network; calculate (206) a difference (140) between the synthetic image and the optical imaging data; and provide (208) a warning signal (142) if the difference differs by a predetermined threshold. The generator neural network is trained to generate a synthetic image (138) of the subject on the subject support in response to inputting an initial vector.

13 Claims, 6 Drawing Sheets

(52) U.S. Cl.
CPC ............ *A61B 5/742* (2013.01); *A61B 5/7405* (2013.01); *A61B 5/0035* (2013.01); *A61B 5/0077* (2013.01); *G06T 2207/20224* (2013.01)

(56) References Cited

U.S. PATENT DOCUMENTS

| | | | |
|---|---|---|---|
| 10,856,832 B2* | 12/2020 | Quan | G16H 30/20 |
| 10,881,353 B2* | 1/2021 | Shoudy | A61B 6/547 |
| 11,083,428 B2* | 8/2021 | Tsukagoshi | A61B 6/469 |
| 11,101,025 B2* | 8/2021 | Popescu | A61N 5/1049 |
| 2005/0265516 A1 | 12/2005 | Haider | |
| 2013/0342851 A1 | 12/2013 | Dresel et al. | |
| 2016/0109545 A1* | 4/2016 | Forthmann | G06T 7/73 382/131 |
| 2016/0128666 A1 | 5/2016 | Grasruck | |
| 2017/0136261 A1 | 5/2017 | Hofman et al. | |
| 2017/0249423 A1 | 8/2017 | Wang | |
| 2017/0311841 A1 | 11/2017 | Rothgang | |
| 2017/0319814 A1* | 11/2017 | Giap | A61B 5/11 |
| 2017/0354385 A1 | 12/2017 | Lerch | |
| 2020/0138395 A1* | 5/2020 | Tsuchiya | A61B 6/589 |
| 2020/0258243 A1* | 8/2020 | Chang | A61B 5/7267 |
| 2020/0268339 A1* | 8/2020 | Hao | G06T 7/73 |
| 2021/0093221 A1* | 4/2021 | Harder | A61B 5/704 |
| 2021/0106303 A1* | 4/2021 | Ishii | G06T 7/50 |
| 2021/0128084 A1* | 5/2021 | Dai | A61B 5/024 |
| 2021/0153767 A1* | 5/2021 | Dai | A61B 5/0064 |
| 2021/0244283 A1* | 8/2021 | Krueger | G06T 7/0016 |

OTHER PUBLICATIONS

Ma et al "Pose Guided Person Image Generation" retrieved from the internet URL:https://papers.nips.cc/paper/6644-pose-guided person image generation.pdf p. 1-4.

International Search Report and Written Opinion from PCT/EP2019/084969 dated Jun. 25, 2020.

Donahue, Jeff, et al.. "Adversarial Feature Learning." published as a conference paper at ICLR 2017.

Schlegl, Thomas, et al. "Unsupervised anomaly detection with generative adversarial networks to guide marker discovery." International Conference on Information Processing in Medical Imaging. 2017.

Goodfellow, Ian, et al. "Generative adversarial nets." Advances in neural information processing systems. 2014.

\* cited by examiner

AUTOMATED DETECTION OF ABNORMAL SUBJECT CONFIGURATION FOR MEDICAL IMAGING

CROSS REFERENCE TO RELATED APPLICATIONS

This application is a U.S. national phase application of International Application No. PCT/EP2019/084969 filed on Dec. 12, 2019, which claims the benefit of EP Application Serial No. 18214629.0 filed on Dec. 20, 2018 and is incorporated herein by reference.

TECHNICAL FIELD OF THE INVENTION

The invention relates to medical imaging.

BACKGROUND OF THE INVENTION

In various medical imaging modalities such as Magnetic Resonance Imaging (MRI), Computer Tomography (CT), Positron Emission Tomography (PET), and others a subject is positioned within the medical imaging system and data is acquired which is descriptive of the subject's internal anatomy. In many cases the proper positioning and configuration of the subject can be complicated.

For example, configuring a subject for a MRI protocol can be complicated: Both the equipment and the subject should be in the proper position. In many MRI protocols, a surface coil or antenna is placed on the subject correctly. The subject may be given a squeeze ball which can be used to alert the operator of a problem. The subject also must take care to be in the proper position. If equipment is not positioned properly or is omitted the subject can be in an unsafe situation and/or the imaging protocol can fail.

United States patent application publication US 2013/0342851 discloses a method for gathering information relating to at least one object positioned on a patient positioning device of a medical imaging device is provided. The method includes the following steps: gathering by optical means of 3-D image data relating to the object positioned on the patient positioning device by means of a 3-D image data recording unit, transferring the gathered 3-D image data from the 3-D image data recording unit to an evaluating unit, determining information relating to the object positioned on the patient positioning device based on the 3-D image data by means of the evaluating unit, generating output information based on the determined information relating to the object positioned on the patient positioning device, and outputting the output information relating to the object positioned on the patient positioning device.

SUMMARY OF THE INVENTION

The invention provides for a medical instrument, a method and a computer program product in the independent claims. Embodiments are given in the dependent claims.

As was mentioned above the proper configuration of a subject prior to the execution of a medical imaging protocol can be complicated. Embodiments may provide for a means of automatically checking the configuration of a subject. This may be performed by training a generator neural network to generate synthetic images of the subject on a subject support. The generator neural network is trained using images where the subject is correctly configured and/or positioned for medical imaging. An optical imaging system acquires optical imaging data of the subject on the subject support. The generator neural network is then used to generate a pseudo image of the subject on the subject support that is as close as possible to the real image of the subject on the subject support. If the subject is not positioned correctly and/or the equipment around the subject is not configured properly the generator neural network will produce a synthetic image that differs from the optical imaging data by a predefined threshold. This then enables the automatic detection if the configuration of the subject is not correct.

In one aspect the invention provides for a medical instrument that comprises a medical imaging system configured for acquiring medical imaging data from a subject. The medical instrument further comprises a subject support configured for supporting the subject during the acquisition of the medical imaging data. The medical instrument further comprises an optical imaging system configured for acquiring optical imaging data of the subject on the subject support. The optical imaging system may be alternatively described as a system for imaging or making optical images of the subject while the subject is on the subject support.

The medical instrument further comprises a memory storing machine-executable instructions and a generator neural network. The generator neural network is trained to generate an artificial image of the subject on the subject support in response to inputting an initial vector.

The medical instrument further comprises a processor. Execution of the machine-executable instructions causes the processor to control the optical imaging system to acquire the optical imaging data. Execution of the machine-executable instructions further causes the processor to generate an initial vector using the optical imaging data. Execution of the machine-executable instructions further causes the processor to generate the artificial image by inputting the initial vector into the generator neural network. Execution of the machine-executable instructions further causes the processor to calculate a difference between the artificial image and the optical imaging data. The difference may for example be a statistical difference or it may be an actual difference related to various pixels or representations of the image:

In one example the term "difference" could be a statistical comparison between the artificial image and the optical imaging data, such as the application of a similarity measure.

In another example the term difference could be a quantity or property related to a difference image calculated between the optical imaging data and the artificial image. For example, the difference image could be thresholded to look for pixels above or below a predetermined value. The difference could also be the presence of a chosen number of pixels being above or below the predetermined value. In another example the difference could be the presence or regions of pixels with a chosen size that are above or below the predetermined value.

Execution of the machine-executable instructions further causes the processor to provide a warning signal if the difference differs by a predetermined threshold. The warning signal could take different forms in different examples. In some instances, it may be an optical, audible or display displayed on a graphical user interface. In other examples the warning signal may be a signal which is provided to various software components or algorithms.

As mentioned above the difference may be a statistical quantity in some examples. For example, the difference could be a correlation or a measure of similarity between the artificial image and the optical imaging data.

In another embodiment the calculation of the difference between the artificial image and the optical imaging data is the calculation of a difference image constructed by subtracting one of the artificial images and the optical imaging data from the other.

In another embodiment execution of the machine-executable instructions further causes the processor to control the medical imaging system to acquire the medical imaging data if the difference is within or allowed by the predetermined threshold. For example, it may be below the predetermined threshold.

In another embodiment execution of the machine-executable instructions further causes the processor to reconstruct a medical image from the medical imaging data if the medical imaging data has been acquired.

In another embodiment the difference is a correlation.

In another embodiment the difference is a difference image calculated by subtracting the artificial image from the optical imaging data or the other way around. The warning signal is provided in response to at least a portion of the difference image differing by the predetermined threshold.

In another embodiment the warning signal is a rendering of the difference image on a display.

In another embodiment the warning signal is an audible signal.

In another embodiment the warning signal is an activation of a warning light.

In another embodiment the warning signal is a rendering of the optical imaging data with a highlighted portion. The highlighted portion is identical with the portion of the difference image that differs by the predetermined threshold.

In another embodiment execution of the machine-executable instructions further causes the processor to train the generator neural network using a generative adversarial network. The generator neural network is trained using additional optical imaging data acquired during acquisition of additional medical imaging data.

In another embodiment execution of the machine-executable instructions further causes the processor to generate a random vector. Execution of the machine-executable instructions further causes the processor to generate an intermediate image by feeding the random vector into the generator neural network. Execution of the machine-executable instructions further causes the processor to calculate the initial vector using the intermediate image and the optical imaging data. This embodiment may be advantageous because it may provide for an automatic means of providing for the initial vector.

The process by which the initial vector is calculated by using the random vector and then generating the intermediate image may be repeated multiple times such that it is an iterative process.

In another embodiment the initial vector is calculated using a search algorithm to iteratively modify elements of the random vector. This embodiment may be used for searching for the best possible initial vector by making incremental changes in the initial vector that is used.

In another embodiment the initial vector is calculated using backpropagation-based gradients to modify the elements of the random vector. For example, an optimization algorithm like stochastic gradient descent may be used to modify elements of the random vector. The techniques that are used for example in deep learning may be used to back propagate and modify the input vector instead of modifying the neural network. This may provide for a rapid means of calculating the initial vector. Such a process may also be done iteratively, where a first random vector is used to produce a better vector which is then repeatedly subjected to back propagations until the answer converges to a solution.

In another embodiment the memory further stores a trained encoder neural network. The initial vector is generated by inputting the optical imaging data into the trained encoder neural network. The trained encoder neural network may be a convolutional neural network which has been trained to generate the vectors which are input into the generator neural network. The trained encoder neural network could for example be part of the generative adversarial network. It could be trained similarly to the generator of discriminator of the GAN. For example, the trained encoder neural network could be trained using backpropagation and stochastic gradient descent.

The encoder neural network and the generator neural network may be two separate neural networks. They could also be incorporated into a single neural network which is similar to an auto encoder convolutional neural network which is typically used for image processing or image modification. A point to notice is that an auto encoder or a trained encoder neural network that has been trained to encode only correct images should not be able to produce an image which contains errors. For example, if an object which is not allowed to be placed into the magnetic resonance imaging system or medical imaging system is with the subject and there has been no images which show this object, then the auto encoder convolutional neural network or the trained encoder neural network may then likely produce a noise-like vector, which will be fed to the Generator. The generator will then produce an image that fails to reproduce this object. This would lead to a large difference between the artificial image and the optical imaging data.

In another embodiment the medical imaging system comprises an X-ray system or a digital X-ray system.

In another embodiment the medical imaging system comprises a computer tomography system.

In another embodiment the medical imaging system comprises a positron emission tomography system.

In another embodiment the medical imaging system comprises a single photon emission tomography system.

In another embodiment the medical imaging system is a magnetic resonance imaging system.

In another embodiment the magnetic resonance imaging system comprises a main magnet configured for receiving the subject. The optical imaging system is configured for acquiring at least a portion of the optical imaging data when the subject is within the main magnet. For example, the main magnet may generate a region which has a magnetic field uniform enough for performing magnetic resonance imaging. This may be referred to as an imaging zone. The optical imaging system may be configured such that at least a portion of the optical imaging data is acquired when the subject is within the imaging zone of the main magnet. This may be advantageous because the warning signal can be provided if the subject goes into an unsafe position or drops something or is otherwise in a configuration which is not suitable or unsafe for performing magnetic resonance imaging.

In another embodiment the medical imaging system is configured for acquiring the medical imaging data from a medical imaging zone. The subject support is configured for transporting the subject to the medical imaging zone. The medical instrument is configured for providing the warning signal before transporting the subject to the medical imaging zone. The medical imaging zone may be considered to be the region in space where the medical imaging system is able to acquire the medical imaging data. For a magnetic resonance imaging system, the medical imaging zone would be the imaging zone as was described in the previous embodiment.

In another embodiment the optical imaging system comprises at least one camera.

In another embodiment the optical imaging system comprises at least one three-dimensional camera.

In another aspect the invention provides for a computer program product comprising machine-executable instructions for execution by a processor controlling the medical instrument. The computer program product further comprises an implementation of a generator neural network. The generator neural network is trained to generate an artificial image of the subject on the subject support in response to an initial vector. The medical instrument comprises a medical imaging system configured for acquiring medical imaging data from a subject.

The medical instrument further comprises a subject support configured for supporting the subject during acquisition of the medical imaging data. The medical instrument further comprises an optical imaging system configured for acquiring optical imaging data of the subject on the subject support. Execution of the machine-executable instructions causes the processor to control the optical imaging system to acquire the optical imaging data. Execution of the machine-executable instructions further causes the processor to generate an initial vector using the optical imaging data.

Execution of the machine-executable instructions further causes the processor to generate the artificial image by inputting an initial vector into the generator neural network. Execution of the machine-executable instructions further causes the processor to calculate a difference between the artificial image and the optical imaging data. Execution of the machine-executable instructions further causes the processor to provide a warning signal response if the difference exceeds a predetermined threshold.

In another aspect the invention provides for a method of operating a medical instrument. The medical instrument comprises a medical imaging system configured for acquiring medical imaging data from a subject within an imaging zone. The medical instrument further comprises a subject support configured for supporting the subject during the acquisition of the medical imaging data. The medical instrument further comprises an optical imaging system configured for acquiring optical imaging data of the subject on the subject support.

The method comprises controlling the optical imaging system to acquire the optical imaging data. The method further comprises generating an initial vector using the optical imaging data. The method further comprises generating the artificial image by inputting an initial vector into a generator neural network. The generator neural network is trained to generate the artificial image of the subject on the subject support in response to inputting the initial vector. The method further comprises calculating a difference between the artificial image and the optical imaging data. The method further comprises providing a warning signal if the difference exceeds a predetermined threshold.

In another embodiment the method further comprises training the generator network using a generative adversarial network with additional optical imaging data acquired during successful acquisition of additional medical imaging data.

It is understood that one or more of the aforementioned embodiments of the invention may be combined as long as the combined embodiments are not mutually exclusive.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid-state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example, a data may be retrieved over a modem, over the internet, or over a local area network. Computer executable code embodied on a computer readable medium may be transmitted using any appropriate medium, including but not limited to wireless, wire line, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage is any non-volatile computer-readable storage medium. In some embodiments, computer storage may also be computer memory or vice versa.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object-oriented programming language such as Java, Smalltalk, C++ or the like and conventional procedural programming languages, such as the "C" programming language or similar programming languages and compiled into machine executable instructions. In some instances, the computer executable code may be in the form of a high-level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It is understood that each block or a portion of the blocks of the flowchart, illustrations, and/or block diagrams, can be implemented by computer program instructions in form of computer executable code when applicable. It is further under stood that, when not mutually exclusive, combinations of blocks in different flowcharts, illustrations, and/or block diagrams may be combined. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, pedals, wired glove, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bi-stable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

Medical image data is defined herein as two- or three-dimensional data that has been acquired using a medical imaging system or scanner. A medical imaging system is defined herein as an apparatus adapted for acquiring information about the physical structure of a patient and construct sets of two dimensional or three dimensional medical image data. Medical image data can be used to construct visualizations which are useful for diagnosis by a physician. This visualization can be performed using a computer.

Magnetic Resonance (MR) data or magnetic resonance imaging data is defined herein as being the recorded measurements of radio frequency signals emitted by atomic spins using the antenna of a Magnetic resonance apparatus during a magnetic resonance imaging scan. MRF magnetic resonance data is magnetic resonance data. Magnetic resonance data is an example of medical image data. A Magnetic Resonance Imaging (MRI) image or MR image is defined herein as being the reconstructed two- or three-dimensional visualization of anatomic data contained within the magnetic resonance imaging data. This visualization can be performed using a computer.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
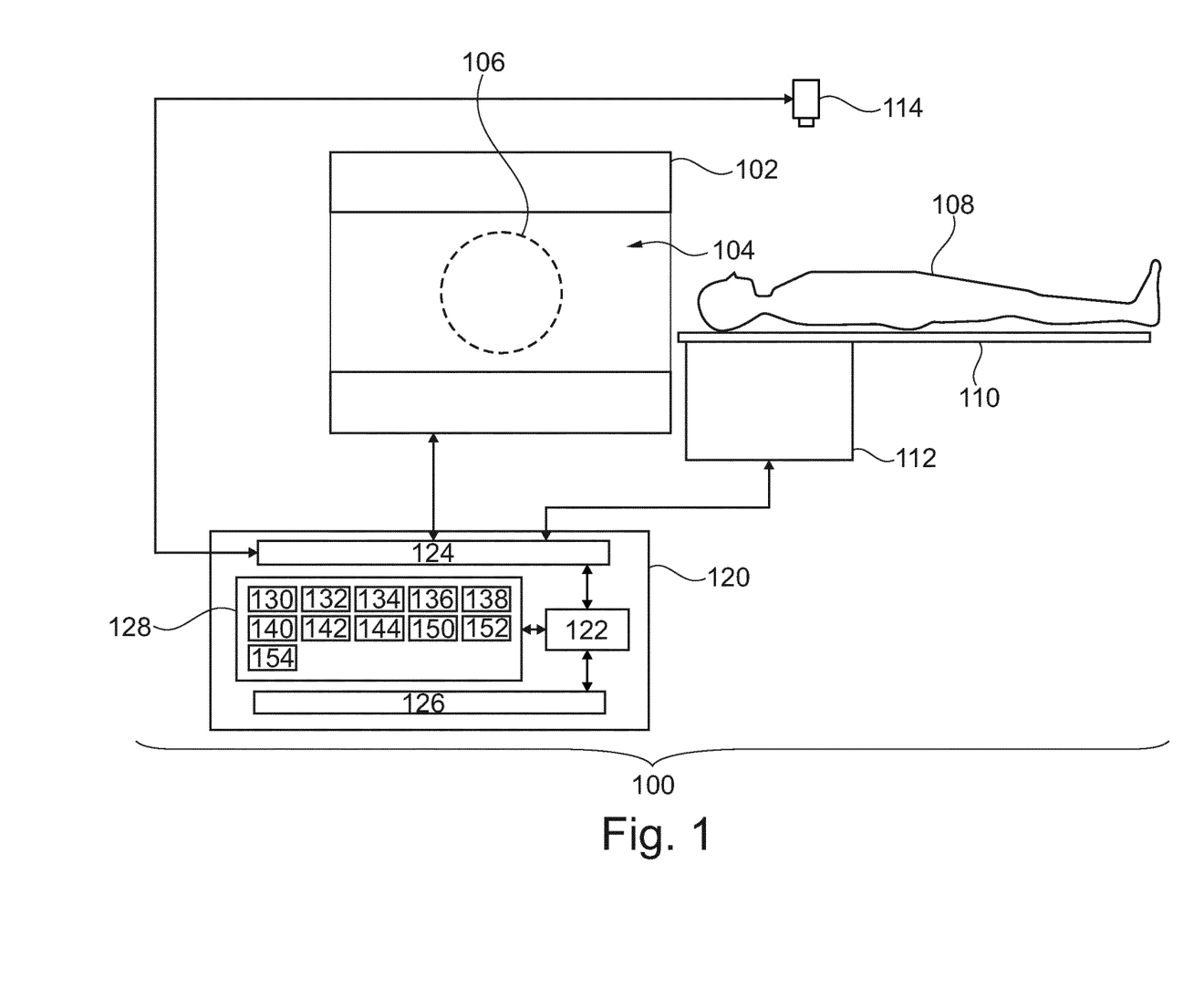
FIG. 1 illustrates an example of a medical instrument.

FIG. 1 illustrates an example of a medical instrument 100. The medical instrument 100 is shown as comprising a medical imaging system 102. The medical imaging system 102 is intended to represent one of a variety of types of medical imaging systems. For example, it may be a magnetic resonance imaging system, a computer tomography system, an X-ray system, a digital X-ray system, a fluoroscope, a single photon emission tomography system, a positron emission tomography system or other similar medical imaging system. In this example the medical imaging system 102 has a cylindrical structure and has a bore 104 into which a subject 108 can be placed. The medical imaging system 102 has a medical imaging zone 106 which is a spatial region from which the medical imaging system 102 is able to acquire medical imaging data. The subject 108 is shown as reposing on a subject support 110. The subject support 110 has an optional actuator 112 which is functional for moving the subject support 110 in order to place at least a portion of the subject 108 within the medical imaging zone 106. Depicted above the subject 108 is an optical imaging system 114. The optical imaging system 114 is able to image at least a portion of the subject 108 when the subject is on the subject support 110.

The medical instrument 100 is further shown as comprising a computer 120. The computer 120 comprises a processor 122 that is in communication with a hardware interface 124, an optional user interface 126, and a memory 128. The hardware interface 124 may be a network or other connection which enables the processor 122 to send and receive commands and/or data with the other components of the medical instrument 100. The memory 128 may be any combination of memory which is accessible to the processor 122.

The optical imaging system 112, the medical imaging system 102, and the subject support 110 are all shown as being connected to the hardware interface 124. The user interface may be any sort of user interface which enables a subject to control and/or receive data or information from the medical instrument 100. For example, the user interface 126 may be used for displaying or providing a warning signal.

The memory 128 is shown as containing machine-executable instructions 130. The machine-executable instructions 130 contain commands which enable the processor 122 to control the operation and function of the medical instrument 100. The memory 128 is further shown as containing a generator neural network 132. The generator neural network 132 is trained to generate an artificial image of the subject on the subject support 110 in response to inputting an initial vector 136. The memory 128 is further shown as containing optical imaging data 134. The memory 128 is further shown as containing the optimized vector 136 that has been created or generated using the optical imaging data 134.

The memory 128 is further shown as containing an artificial image 138 that has been generated by inputting the initial vector 136 into the generator neural network 132. The machine-executable instructions 130 then contain commands which enable the processor 122 to compute a difference 140 between the artificial image 138 and the optical imaging data 134. This may be a statistical value such as a correlation or it may be for example an optional difference image. The memory 128 is further shown as containing a warning signal 142 which is generated or provided when the difference 140 differs by a predetermined threshold 144. The warning signal 142 and the predetermined threshold 144 are shown as also being stored in the memory 128.

The memory 128 is further shown as containing an optional random vector 150 and an optional intermediate image 152. In the generation of the initial vector 136 there may be a process where a random vector 150 is first generated. The random vector 150 is then input into the generator neural network 132 to create and intermediate image 152. The intermediate image may then be used to generate or create the initial vector 136. This can be accomplished in a variety of ways. For example, a brute force search algorithm may be used to iteratively modify elements of the random vector 150 to approach a solution to the initial vector 136. In another example the back-propagation scheme which is normally used to train a neural network using deep learning may be used by freezing the elements of the neural network and then using the back propagation to modify the random vector 150 into the initial vector 136. Both processes may be done iteratively.

In another example the memory 128 may contain an optional trained encoder neural network 154. In this example the trained encoder neural network 154 is trained to receive the optical imaging data 134 as input and then directly output the initial vector 136.

If the warning signal 142 is generated it may take a variety of different forms. There may be an optical, audible or graphic display which is provided to the operator of the medical instrument 100. In other examples the warning signal 142 may be a software or other signal which is transported to another machine or to a software component which triggers an action.

Figure 2:
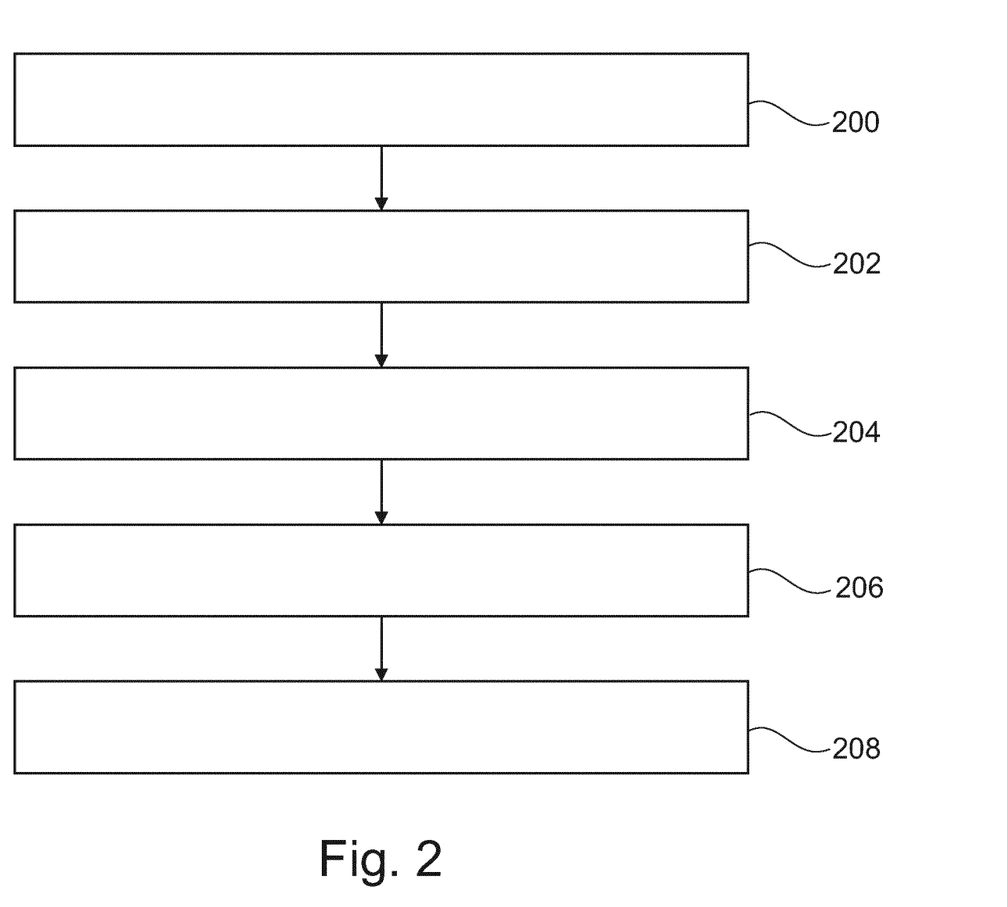
FIG. 2 shows a flow chart which illustrates an example of operating the medical instrument of FIG. 1.

FIG. 2 shows a flowchart which illustrates a method of operating the medical instrument 100 of FIG. 1. First in step 200 the processor controls the optical imaging system 114 to acquire the optical imaging data 134. Next in step 202 the processor generates an initial vector 136 using the optical imaging data 134. This may be accomplished in a variety of ways such as using a neural network to do this or using an iterative process using trial vectors that are input into the generator neural network. Next the method proceeds to step 204. In step 204 an artificial image 138 is generated by inputting the initial vector 136 into the generator neural network 132. Next in step 206 a difference 140 between the artificial image 138 and the optical imaging data 134 is calculated. Finally, in step 208, a warning signal 142 is provided if the difference 140 differs by more than a predetermined threshold 144.

Figure 3:
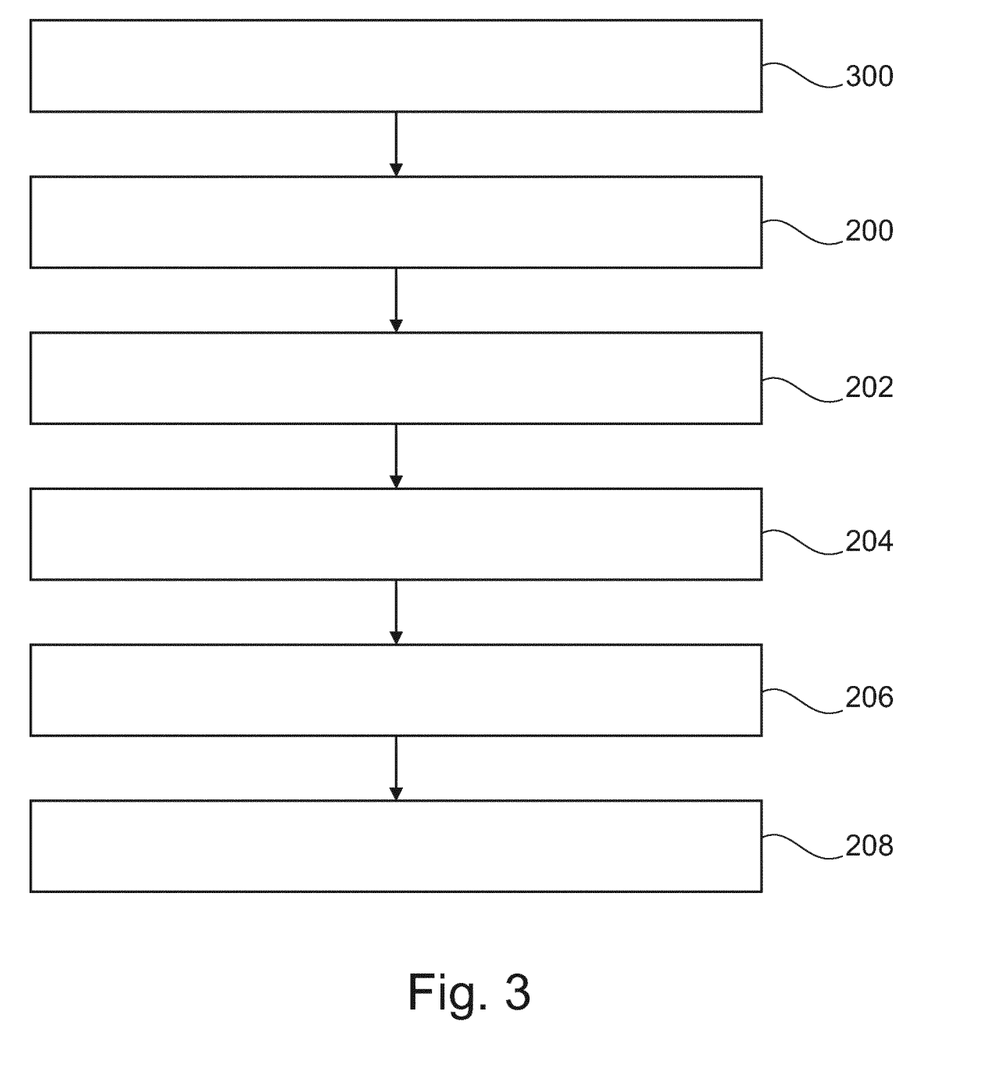
FIG. 3 shows a flow chart which illustrates a further example of operating the medical instrument of FIG. 1.

FIG. 3 shows a further method of operating the medical instrument 100 of FIG. 1. In this method the method starts with step 300. In step 300 the processor trains the generator neural network 132 using a generative adversarial network. The generator neural network is trained using additional optical imaging data acquired during acquisition of additional medical imaging data. This training data and the generative adversarial network may be stored in the memory 128 or may be performed before or after use of the medical instrument 100. The training may also be performed on a different or separate computer system.

Figure 4:
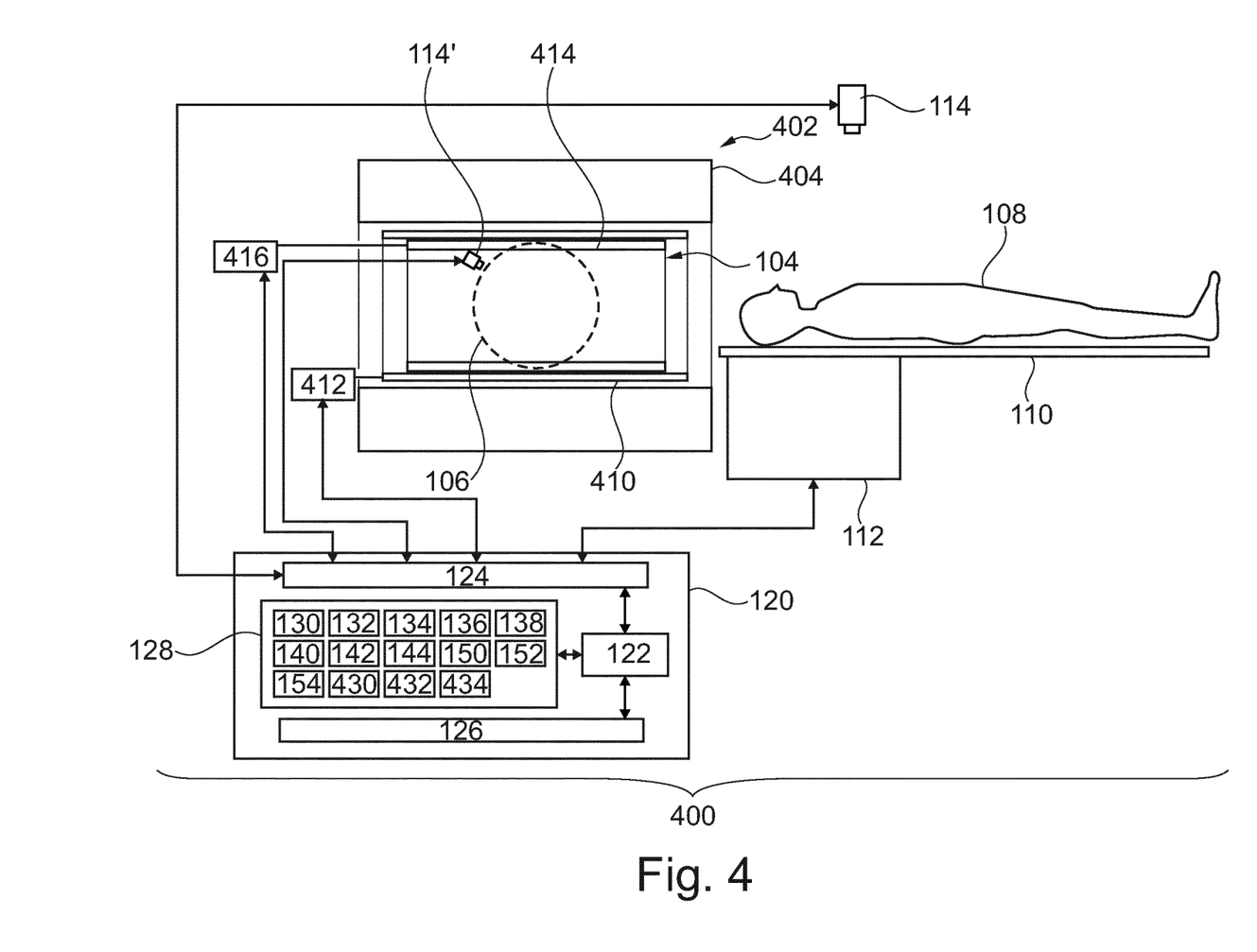
FIG. 4 illustrates a further example of a medical instrument.

FIG. 4 illustrates a further example of a medical instrument 400. In this example the medical imaging system is a magnetic resonance imaging system 402. The magnetic resonance imaging system 402 comprises a magnet 404. The magnet 404 is a superconducting cylindrical type magnet with a bore 406 through it. The use of different types of magnets is also possible; for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils. Within the bore 406 of the cylindrical magnet 404 there is an imaging zone 408 where the magnetic field is strong and uniform enough to perform magnetic resonance imaging. A region of interest 409 is shown within the imaging zone 408. The magnetic resonance data that is acquired typically acquired for the region of interest. A subject 108 is shown as being supported by a subject support 110 such that at least a portion of the subject 108 is within the imaging zone 408 and the region of interest 409.

Within the bore 406 of the magnet there is also a set of magnetic field gradient coils 410 which is used for acquisition of preliminary magnetic resonance data to spatially encode magnetic spins within the imaging zone 408 of the magnet 404. The magnetic field gradient coils 410 connected to a magnetic field gradient coil power supply 412. The magnetic field gradient coils 410 are intended to be representative. Typically magnetic field gradient coils 410 contain three separate sets of coils for spatially encoding in three orthogonal spatial directions. A magnetic field gradient power supply supplies current to the magnetic field gradient coils. The current supplied to the magnetic field gradient coils 510 is controlled as a function of time and may be ramped or pulsed.

Adjacent to the imaging zone 408 is a radio-frequency coil 414 for manipulating the orientations of magnetic spins within the imaging zone 408 and for receiving radio transmissions from spins also within the imaging zone 408. The radio frequency antenna may contain multiple coil elements. The radio frequency antenna may also be referred to as a channel or antenna. The radio-frequency coil 414 is connected to a radio frequency transceiver 416. The radio-frequency coil 414 and radio frequency transceiver 416 may be replaced by separate transmit and receive coils and a separate transmitter and receiver. It is understood that the radio-frequency coil 414 and the radio frequency transceiver 416 are representative. The radio-frequency coil 414 is intended to also represent a dedicated transmit antenna and a dedicated receive antenna. Likewise the transceiver 416 may also represent a separate transmitter and receivers. The radio-frequency coil 414 may also have multiple receive/transmit elements and the radio frequency transceiver 416 may have multiple receive/transmit channels. For example if a parallel imaging technique such as SENSE is performed, the radio-frequency could 414 will have multiple coil elements.

In this example the subject, 108 is positioned such that the subject's head region is within the region of interest 409. In other examples, other parts of the subject's 108 body may be positioned in the region of interest 409.

The transceiver 416, the optical imaging system 114 and 114', and the gradient controller 412 are shown as being connected to a hardware interface 124 of the computer system 120. The optical imaging system 114 comprises a camera outside of the magnet 404 and optionally a camera 114' within the magnet. The camera 114' within the bore 104 is mounted adjacent to so that it is able to image the medical imaging zone 106. The optical imaging system 114' can also be placed within the imaging zone 106.

The memory is further shown as containing pulse sequence commands 430. The pulse sequence commands 430 enable the processor 122 to control the magnetic resonance imaging system 402 to acquire magnetic resonance imaging data 432. The memory 128 is shown as containing pulse sequence commands 430 that have been acquired by controlling the magnetic resonance imaging system 402 with the pulse sequence commands 430. The memory 128 is further shown as containing a magnetic resonance image 434 that has been reconstructed from the magnetic resonance imaging data 432.

The optical imaging system 114 is outside of the magnet 404. It is able to image the subject 108 reposing on the subject support 110 before the subject 108 has been placed into the bore 104 of the magnet 404. The difference 140 can be used to determine if the subject 108 and accompanying equipment such as a warning device or coils or pillows or other objects are configured properly. If no warning signal 142 is present then the subject 108 may be moved by the support 110 into the imaging zone 106 and the magnetic resonance imaging data 432 may be acquired. In this configuration shown in FIG. 4 the position and configuration of the subject is checked before the subject is placed into the magnet 404.

Figure 5:
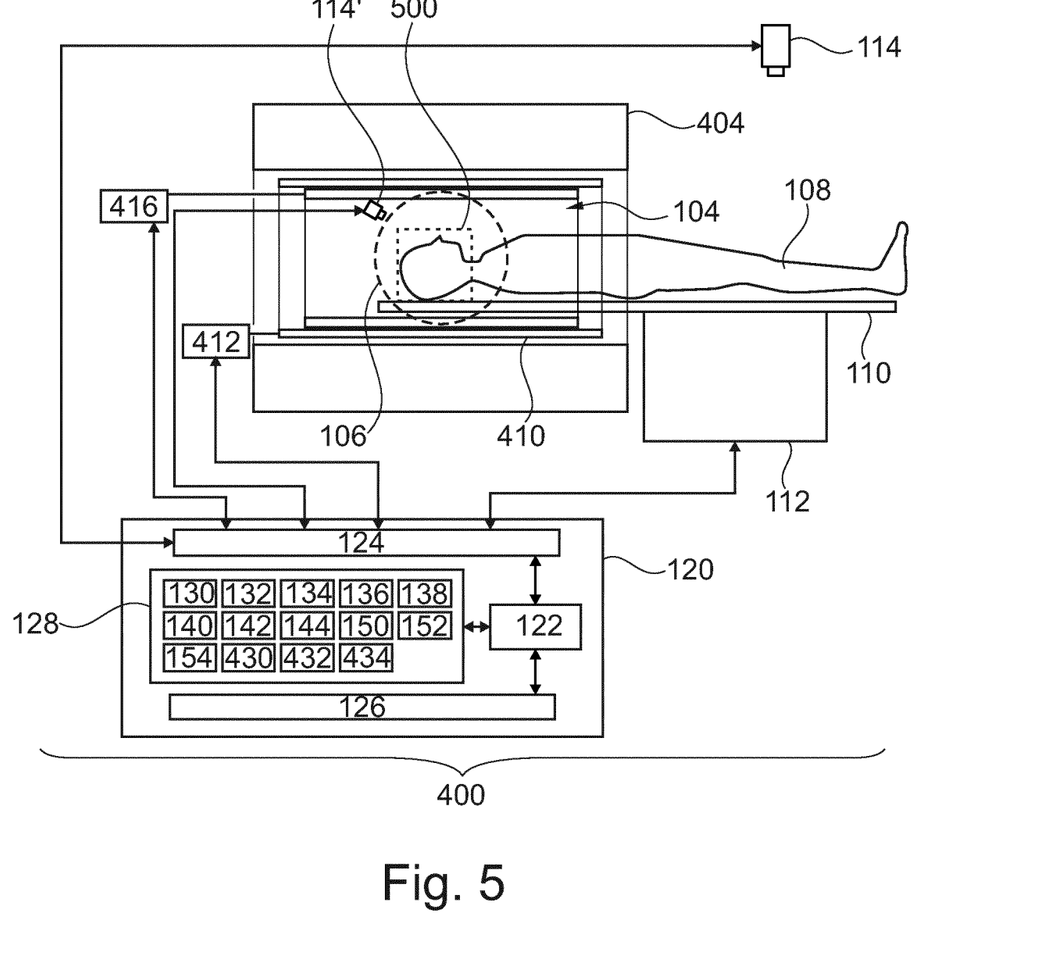
FIG. 5 shows a further view of the medical instrument of FIG. 4.

FIG. 5 illustrates the same medical instrument 400 as was illustrated in FIG. 4. However, in this case, the subject 108 has been placed such that a portion of the subject 108 is within the imaging zone 106. The magnetic resonance imaging data 432 can be acquired representing a region of interest 500.

In this example the optical imaging system 114' within the bore 104 can be used to image the subject 108 before, during and after the acquisition of the magnetic resonance imaging data 432. This for example could be used to determine if the subject 108 is still currently in a configuration for which the magnetic resonance imaging data 432 can be acquired. For example, a surface coil or other fixture may be in a wrong position or the subject may have dropped a signaling device for signaling the operator in the case of emergency.

Examples may provide for a method for fully automatic detection of abnormal events during MM preparation is proposed. It may use a camera to monitor the patient bed area and a detection software based on a Generative Adversarial Network. During training, the generative part of this neural network is trained to synthetize all possible variations of "normal" images. During application, a query image is analyzed by finding the network-created image that is most similar to the query image. In case of abnormal events, substantial differences between network-created and query image can be found, which can be used to localize the abnormality.

In clinical practice, preparation of an MR examination is a time-consuming and error-prone task. The main task of the operator is to help the patient on the MR bed, place the required coils and additional devices (ear protection, nurse bell, physiology sensors, . . . ) and position the light visor at the correct anatomical position. In addition, the operator should detect any abnormal events or configuration during the setup, including lack of headphones, lack of nurse call, inappropriate placement of the coil, incorrect connection of the coil to the socket in the table, cable loops, body loops, etc.

Non-detection of any of these events will typically create substantial delays in the workflow, and may pose patient safety risks in some cases.

Examples may use a camera which is placed such that the patient bed area can be monitored during patient set-up. The images produced by the camera are then analyzed using a Generative Adversarial Network (GAN) to detect any abnormal events or configurations.

Some embodiments may contain one or more of the following features;

First, a large dataset of "normal" images (or image series) is generated, i.e. of images without abnormal events/configurations during set-up. Ideally, this dataset should cover the entire range of typical exams, patient body shapes, poses, etc. Metadata indicating the clinical context of the exam, such as gender, age, body region to be imaged, etc., as typically available in routine clinical examinations, are included in the dataset. Creation of this dataset can be realized by analyzing a large set of images from the clinical workflow, including the annotation of "normal" exams. It may also be augmented artificially by extracting the patient silhouette from a first set of images, followed by transformations such as translation, rotation, or deformation. After these transformations, the modified patient silhouette can be inserted in an image without patient (i.e., with empty patient bed) to create a transformed training image. Using this procedure, a substantially larger training dataset may be created.

Once a large dataset of "normal" images and metadata is available, the generator network of the GAN is trained to produce images with a realistic appearance and in agreement with the corresponding metadata, while the discriminator network is trained to distinguish these generator-created synthetic images from the real training images. Training of these networks can be realized, e.g., using an alternating scheme for generator and discriminator optimization, and standard stochastic gradient descent. The training is successful once the discriminator is incapable of distinguishing generator-created from real images. The purpose of this training step is to train a generator that can synthesize all possible variations of "normal" images.

During application, an input query image can be analyzed using this pre-trained generator network to detect abnormal events or configurations. To this end, the latent space of the generator is searched to find the generator-created image that is most similar to the query image, given the corresponding metadata. This can be realized using a similarity loss function like mean-squared error and backpropagation, or using a dedicated encoder network. If the query image does not contain abnormal events or configurations, the generator should be able to reproduce the query image. In this case, the difference between query and generator-created image should be negligible. In case of abnormalities, however, the generator cannot reproduce the query image, leading to substantial differences between generator-created and query image. The difference image may also be used to localize the abnormality, and provide this information as feedback to the operator.

Examples may be applied to all or to a subset of the frames of the camera video stream, thereby allowing for real-time abnormality detection during the patient set-up. This way, the operator may verify whether a detected abnormal event has been removed. In preferred embodiments, several different networks are trained for different clinical contexts (e.g., abdominal scans with a respiratory belt). The metadata is then used to select the appropriate network for the given exam. Hence, the trained network can be made more specific, thereby reducing the risk to raise a fault alert.

In one example, the camera itself or additional algorithms are capable of providing depth information.

Figure 6:
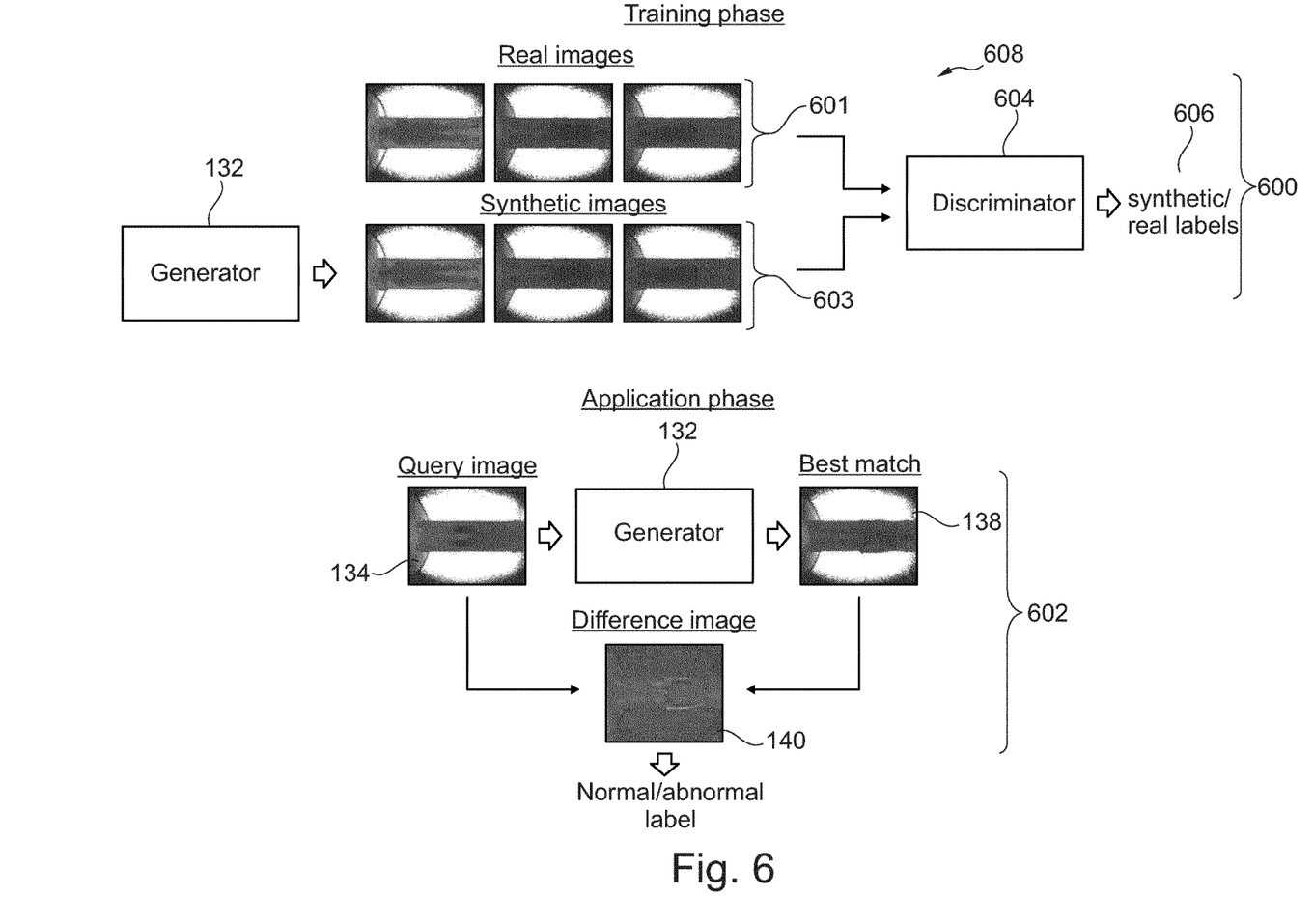
FIG. 6 illustrates method of training a generator neural network.

FIG. 6 illustrates a training phase 600 and an application phase 602 for the generator neural network 132. During training 600, the generator network is trained to create realistic depth images 603, while the discriminator 604 is trained to distinguish these generator-created synthetic images 603 from real ones 601. During application the generator is used to create the image most similar to the input query image. The difference image is then used to detect and localize abnormalities in the query image.

In the training phase 600 a number of additional vectors are input into the generator neural network 132 to produce a number of artificial or synthetic images 603. Another neural network labeled the discriminator 604 compares each of these synthetic images 603 to training optical images 601 and labels the synthetic image 603 as either being synthetic or real. The results of the label 606 are used to both further train the generator 132 and the discriminator 604. This system forms a generative adversarial network 608.

The application phase 602 illustrates the use of the generator neural network 132. The generator neural network 132 outputs the artificial image 138 or best match to the optical imaging data 134. The two images 134 and 138 can be compared to produce a difference 140. In this example it is a difference image.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS 100 medical instrument
102 medical imaging system
104 bore
106 medical imaging zone
108 subject
110 subject support
112 actuator for subject support
114 optical imaging system
114' optical imaging system
120 computer
122 processor
124 hardware interface
126 user interface
128 memory
130 machine executable instructions
132 generator neural network
134 optical imaging data
136 initial vector
138 synthetic image
140 difference between the synthetic image and the optical imaging data
142 warning signal
144 predetermined threshold
150 random vector
152 intermediate image
154 trained encoder neural network
200 control the optical imaging system to acquire the optical imaging data
202 generate an initial vector using the optical imaging data
204 generate the synthetic image by inputting the initial vector into the generator neural network
206 calculate a difference between the synthetic image and the optical imaging data
208 provide a warning signal if the difference differs by a predetermined threshold
300 train the generator neural network using a generative adversarial network
400 medical instrument
402 magnetic resonance imaging system
404 main magnet
410 magnetic field gradient coils
412 magnetic field gradient coil power supply
414 bird cage coil
416 transceiver
430 pulse sequence commands
432 magnetic resonance imaging data
434 magnetic resonance image
500 region of interest
600 training phase
602 application phase
601 additional or training optical image data or images
603 synthetic images
604 discriminator
606 label as real or synthetic
608 generative adversarial network

The invention claimed is:

1. A medical instrument comprising:
a medical imaging system configured to acquiring medical imaging data from a subject;
a subject support configured to support the subject during acquisition of the medical imaging data;
an optical imaging system configured to acquire optical imaging data of the subject on the subject support;
a memory configured to store machine executable instructions and a generator neural network, wherein the generator neural network is trained to generate a synthetic image of the subject on the subject support in response to inputting an initial vector;
a processor, wherein execution of the machine executable instructions causes the processor to:
control the optical imaging system to acquire the optical imaging data;
generate the initial vector using the optical imaging data,
generate the synthetic image by inputting the initial vector into the generator neural network;
calculate a difference between the synthetic image and the optical imaging data; and
provide a warning signal if the difference differs by a predetermined threshold;
wherein the initial vector is generated by any one of the following:
generating a random vector, generating an intermediate image by feeding the random vector into the generator neural network, and calculating the initial vector using the intermediate image and the optical imaging data; and
wherein the memory further stores a trained encoder neural network, wherein the initial vector is generated by inputting the optical imaging data into the trained encoder neural network.

2. The medical instrument of claim 1, wherein the difference is at least one of the following:
a correlation; and
a difference image calculated by subtracting the artificial image from the optical imaging data, wherein the warning signal is provided in response to at least a portion of the difference image differs by the predetermined threshold.

3. The medical instrument of claim 1, wherein the warning signal is at least one of the following:
a rendering of the difference image on a display;
an audible signal;
an activation of a warning light;
a rendering of the optical imaging data with a highlighted portion, where the highlighted portion is identical with the portion of the difference image that differs by the predetermined threshold.

4. The medical instrument of claim 1, wherein execution of the machine executable instructions further causes the processor to train the generator neural network using a generative adversarial network, wherein the generator neural network is trained using additional optical imaging data acquired during acquisition of additional medical imaging data.

5. The medical instrument of claim 1, wherein the initial vector is calculated using any one of the following:
using a search algorithm to iteratively modify elements of the random vector; and
iteratively modifying the elements of the random vector using backpropagation.

6. The medical instrument of claim 1, wherein the medical imaging system comprises at least one of a group including: an x-ray system, a computed tomography system, a positron emission tomography system, a single photon emission tomography system, and combinations thereof.

7. The medical instrument of claim 1, wherein the medical imaging system is a magnetic resonance imaging system.

8. The medical instrument of claim 7, wherein the magnetic resonance imaging system comprises a main magnet configured for receiving the subject, wherein the optical imaging system is configured for acquiring at least a portion of the optical imaging data when the subject is within the main magnet.

9. The medical instrument of claim 1, wherein the medical imaging system is configured for acquiring the medical imaging data from an imaging zone, wherein the subject support is configured for transporting the subject to the medical imaging zone, wherein the medical instrument is configured for providing the warning signal before transporting the subject to the imaging zone.

10. The medical instrument of claim 1, wherein the optical imaging system comprises any one of the following: at least one camera, at least one 3D camera, and combinations thereof.

11. A computer program product comprising machine executable instructions stored on non-transitory computer readable medium for execution by a processor controlling a medical instrument, wherein the computer program product further comprises an implementation of a generator neural network, wherein the generator neural network is trained to generate an synthetic image of the subject on the subject support in response to inputting an initial vector, wherein the medical instrument comprises a medical imaging system configured for acquiring medical imaging data from a subject, wherein the medical instrument further comprises a subject support configured for supporting the subject during acquisition of the medical imaging data, wherein the medical instrument further comprises an optical imaging system configured for acquiring optical imaging data of the subject on the subject support, wherein execution of the machine executable instructions causes the processor to:
 control the optical imaging system to acquire the optical imaging data;
 generate the initial vector using the optical imaging data;
 generate the synthetic image by inputting the initial vector into the generator neural network;
 calculate a difference between the synthetic image and the optical imaging data; and
 provide a warning signal in response if the difference exceeds a predetermined threshold;
 wherein the initial vector is generated by any one of the following:
 generating a random vector, generating an intermediate image by feeding the random vector into the generator neural network, and calculating the initial vector using the intermediate image and the optical imaging data; and
 wherein the memory further stores a trained encoder neural network, wherein the initial vector is generated by inputting the optical imaging data into the trained encoder neural network.

12. A method of operating a medical instrument, wherein the medical instrument comprises a medical imaging system configured for acquiring medical imaging data from a subject within an imaging zone, a subject support configured for supporting the subject during acquisition of the medical imaging data, an optical imaging system configured for acquiring optical imaging data of the subject on the subject support, wherein the method comprises:
 controlling the optical imaging system to acquire the optical imaging data;
 generating the initial vector using the optical imaging data;
 generating the synthetic image by inputting the initial vector into a generator neural network, wherein the generator neural network is trained to generate the synthetic image of the subject on the subject support in response to inputting the initial vector;
 calculating a difference between the artificial image and the optical imaging data; and
 providing a warning signal if the difference exceeds a predetermined threshold;
 wherein the initial vector is generated by any one of the following:
 generating a random vector, generating an intermediate image by feeding the random vector into the generator neural network, and calculating the initial vector using the intermediate image and the optical imaging data; and
 wherein the memory further stores a trained encoder neural network, wherein the initial vector is generated by inputting the optical imaging data into the trained encoder neural network.

13. The method of claim 12, wherein the method further comprises training the generator neural network using a generative adversarial network with additional optical imaging data acquired during successful acquisition of additional medical imaging data.

* * * * *